United States Patent
Chen et al.

(10) Patent No.: US 9,328,141 B2
(45) Date of Patent: May 3, 2016

(54) POLYPEPTIDES FOR THE TREATMENT OR PREVENTION OF CANCER AND USES THEREOF

(75) Inventors: Jianhua Chen, Wuhan (CN); Yi Huang, Wuhan (CN); Junyu Xiong, Wuhan (CN); Caihong Chen, Wuhan (CN)

(73) Assignee: WUHAN KATYGEN PHARMACEUTICALS, INC., Wuhan (CN)

(*) Notice: Subject to any disclaimer, the term of this patent is extended or adjusted under 35 U.S.C. 154(b) by 351 days.

(21) Appl. No.: 13/639,488

(22) PCT Filed: Sep. 29, 2010

(86) PCT No.: PCT/CN2010/077470
§ 371 (c)(1),
(2), (4) Date: Mar. 2, 2013

(87) PCT Pub. No.: WO2011/124063
PCT Pub. Date: Oct. 13, 2011

(65) Prior Publication Data
US 2013/0149372 A1    Jun. 13, 2013

(30) Foreign Application Priority Data
Apr. 7, 2010    (CN) .......................... 2010 1 0140032

(51) Int. Cl.
| | |
|---|---|
| *C07K 7/08* | (2006.01) |
| *C07K 5/00* | (2006.01) |
| *A61K 38/07* | (2006.01) |
| *A61K 38/10* | (2006.01) |
| *C07K 5/103* | (2006.01) |

(52) U.S. Cl.
CPC . *C07K 7/08* (2013.01); *A61K 38/07* (2013.01); *A61K 38/10* (2013.01); *C07K 5/00* (2013.01); *C07K 5/101* (2013.01)

(58) Field of Classification Search
None
See application file for complete search history.

(56) References Cited

FOREIGN PATENT DOCUMENTS

| AU | WO03018630 A1 | 3/2003 |
|---|---|---|
| CN | 1305497 A | 7/2001 |

OTHER PUBLICATIONS

Groner et al (Bioengineered, Dec. 2012, vol. 3, pp. 320-325).*
Voskoglou-Nomikos et al (Clinical Cancer Research, 2003, vol. 9, pp. 4227-4239).*
Cui et al (Journal of Chemical Information and Modeling, 2010, vol. 50, pp. 380-387).*
C. Z Zeng, et al. Identification of tumor progression-related genes in astrocytoma cell lines. Chin J. Clin Oncol. 2008, 5:391-399.

* cited by examiner

*Primary Examiner* — Karen Canella
(74) *Attorney, Agent, or Firm* — CBM Patent Consulting, LLC

(57) ABSTRACT

Disclosed herein are polypeptides or their derivatives and their application. The polypeptides and their derivatives can treat or prevent cancer. The polypeptides of the invention have significant lethality to the cancer cells when used alone. When its clinical commonly used chemotherapy drugs such as cisplatin in combination, it can significantly increase the sensitivity of chemotherapeutic agents on cancer cells, to enhance its lethality of cancer cells, to reduce the dosage. The peptides can kill a variety of cancer cells, but without apparent toxicity enhancing effect on normal cells. The prepared peptides of the present invention can be chemically synthesized, high-purity, low molecular weight, specificity, non-immunogenic, safe and reliable.

1 Claim, 6 Drawing Sheets

```
SEQUENCE LISTING

<160> NUMBER OF SEQ ID NOS: 10

<210> SEQ ID NO 1
<211> LENGTH: 4
<212> TYPE: PRT
<213> ORGANISM: Homo sapiens

<400> SEQUENCE: 1

Ile Val His Asn
1

<210> SEQ ID NO 2
<211> LENGTH: 14
<212> TYPE: PRT
<213> ORGANISM: Homo sapiens

<400> SEQUENCE: 2

Ile Val His Asn Gly Phe Arg Arg Gly Trp Met Trp Gly Gly
1               5                   10
```

```
<210> SEQ ID NO 3
<211> LENGTH: 14
<212> TYPE: PRT
<213> ORGANISM: Homo sapiens

<400> SEQUENCE: 3

Ile Val His Asn Gly Phe Arg Arg Gly Trp Met Trp Ala Glu
1               5                   10

<210> SEQ ID NO 4
<211> LENGTH: 14
<212> TYPE: PRT
<213> ORGANISM: Homo sapiens

<400> SEQUENCE: 4

Ile Val His Asn Gly Phe Arg Arg Gly Trp Met Trp Val Glu
1               5                   10

<210> SEQ ID NO 5
<211> LENGTH: 16
<212> TYPE: PRT
<213> ORGANISM: Homo sapiens

<400> SEQUENCE: 5

Met Phe Ile Val His Asn Glu Leu Arg Arg Gly Trp Trp Trp Ala Glu
1               5                   10                  15

<210> SEQ ID NO 6
<211> LENGTH: 16
<212> TYPE: PRT
<213> ORGANISM: Homo sapiens

<400> SEQUENCE: 6

Met Phe Ile Val His Asn Gly Phe Arg Arg Gly Trp Trp Trp Ala Glu
1               5                   10                  15

<210> SEQ ID NO 7
<211> LENGTH: 16
<212> TYPE: PRT
<213> ORGANISM: Homo sapiens

<400> SEQUENCE: 7

Met Phe Ile Val His Asn Glu Leu Arg Arg Gly Trp Trp Trp Val Glu
1               5                   10                  15

<210> SEQ ID NO 8
<211> LENGTH: 16
<212> TYPE: PRT
<213> ORGANISM: Homo sapiens

<400> SEQUENCE: 8

Met Phe Ile Val His Asn Glu Leu Arg Arg Gly Trp Trp Trp Val Thr
1               5                   10                  15

<210> SEQ ID NO 9
<211> LENGTH: 16
<212> TYPE: PRT
<213> ORGANISM: Homo sapiens

<400> SEQUENCE: 9

Met Phe Ile Val His Asn Gly Phe Arg Arg Gly Glu Met Trp Ala Glu
1               5                   10                  15
```

```
<210> SEQ ID NO 10
<211> LENGTH: 16
<212> TYPE: PRT
<213> ORGANISM: Homo sapiens

<400> SEQUENCE: 10

Met Phe Ile Val His Asn Glu Phe Arg Arg Gly Glu Met Trp Ala Glu
1               5                   10                  15
```

POLYPEPTIDES FOR THE TREATMENT OR PREVENTION OF CANCER AND USES THEREOF

FIELD OF TECHNOLOGY

The present invention relates to polypeptides and their uses, in particular, relates to the polypeptide for the treatment or prevention of cancer as well as derived by the peptide having the treatment or prevention of cancer efficacy. The present invention also relates to the uses of the above polypeptides or their derivatives products in the preparation of antineoplastic, the present invention belongs to the polypeptide of the field of anti-tumor.

BACKGROUND OF THE INVENTION

A research report published by the WHO show that: the situation of global cancer will be increasingly serious. In the next 20 years new cancer patients number will increased by current 10 million per year to 15 million. Thus the cancer deaths increases annually from 6 million to 10 million. The tumor has become one of the major diseases of a serious threat to human safety and health. China's Ministry of Health statistics show that: China's nascent tumors in patients with a total of about 220 million people a year. Which each year there are about 1.21 million patients with malignant newborn accounted annually newborn to 55% of the total number of cancer patients. The same time, about 3.1 million existing tumor patients, malignant tumors around for about 182 million of existing patients, accounting for 58% of the total number of existing cancer patients in China. Cancer has become the main causes of death in China, accounting for more than 20% of the cause of death.

There are three ways in the treatment of malignant tumors: surgery, chemotherapy, radiation therapy, where chemotherapy is the fastest method of treatment in progress in cancer treatment in recent years. However, chemotherapy drugs are often the "right and wrong", "regardless of the enemy", they kill tumor cells while also killing the normal cells of the body. Therapeutic dose toxicity of normal tissues and organs, has brought great suffering to the patient and the poor efficacy, such as bone marrow suppression, gastrointestinal reactions, heart, kidney and other organ damage. Therefore, the study of new anticancer drugs is imperative. Selective regulatory molecules on tumor cell signaling pathways may be a novel research directions of the chemotherapy drugs.

DETAILED DESCRIPTION OF THE INVENTION

The present invention according to the primary sequence of G3BP protein closely related and tumorigenesis, as well as of the protein homologs (PDBID: 1gy5 1gy6), by computer homology modeling method, modeling the three-dimensional structure of the proteinmodel. Based on the protein and its binding protein RasGAP interaction mode, using the principle of molecular dynamics, protein docking, molecular dynamics simulation, molecular simulation methods combined with free energy forecasting, energy decomposition, rational drug design to obtain a series of specifically promotecancer cell apoptosis active polypeptide (Chinese Patent Application No. 200910163852.1) G3BP protein is the target of the present invention. By the the above molecular simulation method, and the polypeptide chemical synthesis, cell biological detection method, we designed synthesized and screened new peptides. According to the previous energy decomposition results, we identify key residues important contribution to protein interactions, and then design the polypeptide sequences of the anti-cancer activity. We carry out the molecular docking calculation between anticancer peptides and G3BP, and then determine the three-dimensional structure of the peptide-protein complexes. The application of the aforementioned methods to carry out the simulation. Polypeptide in accordance with the calculation result of the mutation and activity evaluation, Based on these calculations we have designed a series of polypeptide with better anticancer activity. The polypeptides of the invention have significant lethality to the cancer cells when used alone. When its used with clinical chemotherapy drugs such as cisplatin in combination, it can significantly increase the sensitivity of chemotherapeutic agents on cancer cells, to enhance its lethality of cancer cells, to reduce the dosage. We have proved that the peptides have anti-tumor effects in animal tumor models.

After intensive research, the present inventors found that peptides can achieve the above object, which having the characteristics listed in the following technical features.

A polypeptide which can treat or prevent cancer. Its amino acid sequence is shown as SEQ ID NO.1.

An isolated and purified nucleotide sequence, It can encode the peptide, which peptide's amino acid sequence shown as the SEQ ID NO.1

An isolated and purified nucleotide sequence, It can encode the peptide, which peptide's amino acid sequence shown as formula 1.

An isolated and purified nucleotide sequence, It can encode the peptide, which peptide's amino acid sequence shown as formula 2.

An expression vector, it can encode at least one copy of a polypeptide. The amino acid sequence of the polypeptide is shown as SEQ ID NO.1.

An expression vector, it can encode at least one copy of a polypeptide. The amino acid sequence of the polypeptide is shown as formula 1.

An expression vector, it can encode at least one copy of a polypeptide. The amino acid sequence of the polypeptide is shown as formula 2.

A prokaryotic or eukaryotic host cell, the host cell contains all the expression vector.

The present invention still further provides product obtained by conjugating or mixing the amino acid sequence of SEQ ID NO.1, the general formula 1 or general formula 2 with formulation which can increase the peptide accumulation in cells of the preparation phase.

Said formulation is carrier which can assist the peptide to penetrate the cell membrane. The compound obtained by conjugating or mixing the amino acid sequence of SEQ ID NO.1 general formula 1 or general formula 2 with carrier, which carrier can assist the peptide to penetrate the cell membrane. The carriers are HIV48-57 peptide, FHV-outer 35-49 peptide, HTLV-II Rex 4-16 peptide or BMV gag7-25 peptide. The conjugates can more effective through the cell membrane, having a stronger anti-cancer effect of the partial works in the cancer cells, so it has stronger cytotoxicity to cancer cells.

The formulation, which can conjugate with the peptides of SEQ ID No. 1, formula 1 or formula 2, may be nano-materials, liposomes or oily compounds.

The peptides of SEQ ID NO.1, general formula 1 or general formula 2 are conjugated with the nano-materials, liposomes and other polymer materials. Conjugated compounds of the peptides of the present invention can be more stable to be transported into the target cell in vivo. The present invention peptides can also be mixed with the the oily compound or a mixture of the oily compounds, the mixture can also be obtained so that the peptide of the present invention relates to more stable to be transported into the target cell in vivo.

A pharmaceutical composition of treating or preventing cancer comprises, the composition is composed with an active substance a pharmaceutical effective amount of SEQ ID NO.1, formula 1 or formula 2, wherein the peptide, and a pharmaceutically acceptable carrier, diluent and/or satoagent.

The present invention also provides the SEQ ID NO.1, and the formula 1 or formula 2, wherein the peptide used for the purpose of the preparation of a drug for the treatment or prevention of cancer.

The cancer include but are not limited to: lung cancer, liver cancer, gastric cancer, colon cancer, colorectal cancer, esophageal cancer, breast cancer, leukemia, bladder cancer, cervical cancer and nasopharyngeal cancer.

The present invention also provides the SEQ ID NO.1, and the formula 1 or formula 2, wherein the peptide used for the preparation to enhance the use of genotoxins to selectively kill cancer cells drug.

The cancer include, but are not limited to: lung cancer, liver cancer, gastric cancer, colon cancer, colorectal cancer, esophageal cancer, breast cancer, leukemia, bladder cancer, cervical cancer and nasopharyngeal cancer.

The genotoxins include but are not limited to: cisplatin, oxaliplatin, paclitaxel, epirubicin, doxorubicin, pirarubicin, daunorubicin, mitomycin, dacarbazine, cyclophosphamide, gemcitabine or capecitabine.

The peptides of the invention can be mixed with genotoxins, and then add a pharmaceutically acceptable excipient or carrier. The mixture is made to a new type of more effective anti-cancer drug.

Peptides of the present invention are usually used in an amount to achieve the intended purpose of use. When used for the prevention and treatment of cancer, the peptide or its pharmaceutically acceptable composition is a therapeutically effective amount taken or used. For systemic medication, it is possible according to the in vitro experiments estimate treatment effective amount or dosage. It can also be applied in the art commonly used method to estimate the starting dose in vivo animal models. Of course, the specific effective amount of the peptide of the present invention should depend on the specific treatment object, the body weight of the subject to be treated, the severity of the disease, the mode of administration as well as the attending physician's clinical judgment.

After intensive research, the present inventors found that peptides can prevent and treat cancer. The polypeptides of the invention have significant lethality to the cancer cells when used alone. When used with clinical chemotherapy drugs such as cisplatin in combination, there can significantly increase the sensitivity of chemotherapeutic agents on cancer cells, to enhance its lethality of cancer cells, to reduce the dosage. Peptides of the present invention can kill lung cancer, liver cancer, stomach cancer, colon cancer, colorectal cancer, esophageal cancer, breast cancer, leukemia and other cancer cells. Peptides have no obvious toxic enhancement effect on normal cells. The prepared peptide of the present invention can be chemically synthesized, high-purity, low molecular weight, specificity, non-immunogenic, safe and reliable.

The peptides of the present invention can be used alone for the treatment and prevention of cancer and has a good effect. The peptides can also be combined with chemotherapy drugs (such as cisplatin, paclitaxel, etc.). It can be selectively enhanced chemotherapeutic drugs on the sensitivity of tumor cells, significantly reduced the dose of the chemotherapy drugs, while the toxic effect on normal cells, thereby reduce the toxicity and side effects of chemotherapy drugs.

Figure 1:
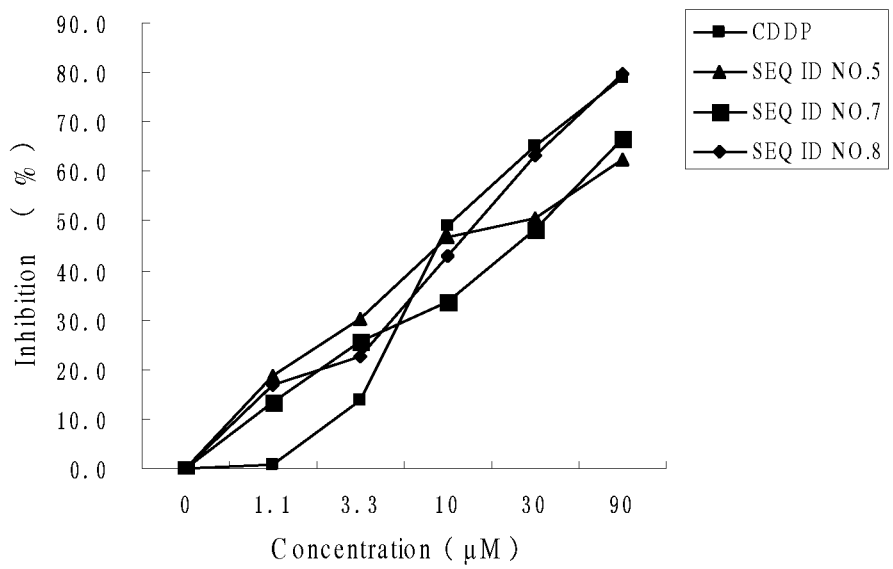
FIG. 1 SEQ ID NO.5, SEQ ID NO.7, SEQ ID NO.8 peptide independently inhibition of human colon cancer cells.

```
Amino acid sequences:
SEQ ID No. 1:      IVHN

SEQ ID No. 2:      IVHNGF RRGWM WGG

SEQ ID No. 3:      IVHNGF RRGWM WAE

SEQ ID No. 4:      IVHNGF RRGWM WVE

SEQ ID No. 5:      MFI VHNEL RRGWW WAE

SEQ ID No. 6:      MFI VHNGF RRGWW WAE

SEQ ID No. 7:      MFI VHNEL RRGWW WVE

SEQ ID No. 8:      MFI VHNEL RRGWW WVT

SEQ ID No. 9:      MFI VHNGF RRGEM WAE

SEQ ID No. 10:     MFI VHNEF RRGEM WAE
```

Below in conjunction with a specific embodiment of the present invention will be described further. The advantages and features of the present invention will be more clearly with the description. However, these embodiments are merely exemplary, and does not constitute any limitation on the scope of the invention Skilled in the area should understand that, details and forms of the technical solution of the present invention without departing from the spirit and scope of the present invention can be modified or replaced. However, these modifications and substitutions fall within the scope of protection of the present invention.

Example 1

The Synthesis of this Polypeptide

1) Apparatus and materials in the experiment dimethylformamide (DMF), piperidine, resin, dichloromethane (DCM), Kaiser kit, 1-hydroxybenzotriazole (HOBt), N,N,N',N'-tetramethyluronium hexanuorophosphate (HBTU), N,N- diisopropylethylamine (DIEA), methanol, all kinds of amino acid, the special tube in solid phase peptide synthesis.

2) Experiment Step

The resin was weighed and put into the special tube in solid phase peptide synthesis (hereafter referred to as a reactor) as well as added DMF. And then the mixture swelled for 10 minutes. After extracting away DMF and de-protection of F-moc removed, the DMF contained 20% piperidine were put into this reactor for fully mixing. 5 minutes later, the solution was moved and add again the DMF contained 20% piperidine to de-protect in 7 minutes.

Extracting the protective solution to use DMF to wash resin 4-5 times and removing DMF to wash with DCM 1-2 times, some resin (about 5-10 mg) were dissociated from the resin to test with Kaiser method and record the reactive colors, and then preparing materials input, the amino acid condensation will be start.

Adding the right amino acid in the light of sequence of SEQ.1-SEQ.9 peptide, HOBt and DMF into a suitable container, after the mixture was completely dissolved, DIEA was added to active for 5 minutes. With that action with HBTU in ice-water bath 5 minutes, the compound was put into reactor and stirred to react.

After 90 minutes, few resin were taken out to test with Kaiser method and record the reactive colors. Removing liquid in the reactor and washing 2 times, the first peptide on resin by amino-condensation was acquired after extracting DMF. The same reaction named 'de-protection with Fomc and amino-condensation' go though the last amino had completed the reaction. And the peptide which sequence number is SEQ ID NO.1-10 was got.

The rejoining SEQ ID NO.1-10 peptide of HIV48-57 is acquired by chemical synthesis, that was using the order method to respectively link the right amino acid and the SEQ ID NO.1-10 peptide, according to the sequence of HIV48-57 peptide. After the reaction, DCM washed resin 2-3 times, that was removed. Then mixing methanol to shrink (5 min+5 min) and removing it, the compound was continued to pumped dry in 15-20 minutes.

Being taken out and transferred to round bottomed flask, The synthetic peptide with resin was pumped dry in dryers and cracked at the room temperature in 2 hours. Through filtering, the resin was lyophilized in the vacuum. This crude peptide was purified by preparative reversed-phase HPLC of shimadzu. The purity of the purified peptide was higher than 90%. At last, the gotten pure peptide was misidentified by mass spectrum (MS, electrospray). The physical and chemical properties of SEQ ID NO.1-SEQ ID NO.10 peptide was as the table 1 showed.

Example 2

The Inhibition of Human Colon Cancer Cell Respectively Induced by SEQ ID NO.5, SEQ ID NO.7 and SEQ ID NO.8 Peptide with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and then cultured at 37° C. with 5% $CO_2$ under saturated humidity for 24 h. They were added into wells, like cisplatin, SEQ ID NO.5, SEQ ID NO.7 and SEQ ID NO.8, that the concentration gradient of them in every mixture always was 90 μmol/L, 30 μmol/L, 10 μmol/L, 3.3 μmol/L, 1.1 μmol/L, 0 μmol/L, with 3 wells for each group. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=($OD$ in control group−$OD$ in experimental group)/$OD$ in control group×100%

2. Experimental Results

According to FIG. 1, each one of SEQ ID NO.5, SEQ ID NO.7 and SEQ ID NO.8 can observably inhibited the human HCT116 cell, especially the effect of that was better than cisplatin. when the concentration of them was lower than 10 μmol/L. The peptides of the present invention used alone have a role to tumor cells, and it can be used as the treatment and prevention of cancer.

Example 2

The Inhibition of Human Colon Cancer Cell Induced by SEQ ID NO. 8 Peptide with MTT Colorimetry 1. Experimental Method The human lung cancer cell line A549 which was bought from China Center For Type Culture Collection were suspended in F-12K medium with 10% heart-inactivated fetal bovine serum, seeded into 96-well plate at a density of 5000-10000 cells per well, and cultured at 37° C. with 5% $CO_2$ under saturated humidity for 24 h. Cisplatin and SEQ ID NO.8 were added into wells, that the concentration gradient of them in every mixture always was 90 μmol/L, 30 μmol/L, 10 μmol/L, 3.3 μmol/L, 1.1 μmol/L, 0 μmol/L, with 3 wells for each group. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=($OD$ in control group−$OD$ in experimental group)/$OD$ in control group×100%

2. Experimental Results

Figure 2:
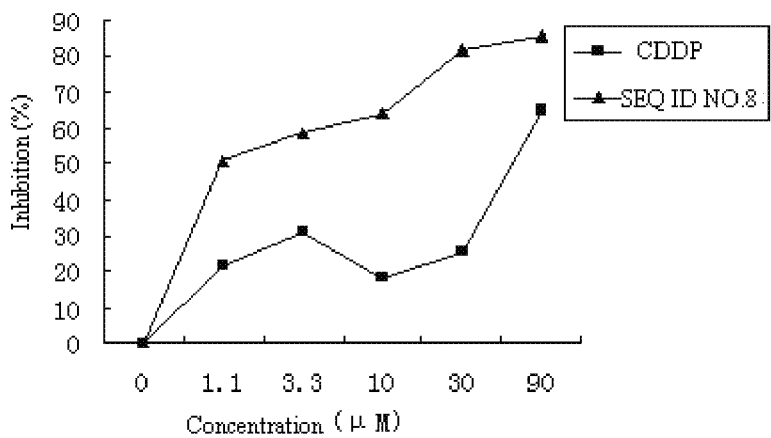
FIG. 2 SEQ ID NO.8 peptide inhibition of human lung cancer cells.

In FIG. 2, SEQ ID NO.8 can observably inhibited the human lung cancer cell A549, which showed this peptide of the invention used alone has a role to tumor cells, and it can be used as the treatment and prevention of cancer.

Example 3

The Combined Effects of SEQ ID NO.1 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, SEQ ID NO.1 and the mixture of the first two were respectively added into wells, that the concentration gradient of them in every mixture always was 90 μmol/L, 30 μmol/L, 10 μmol/L, 3.3 μmol/L, 1.1 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 3:
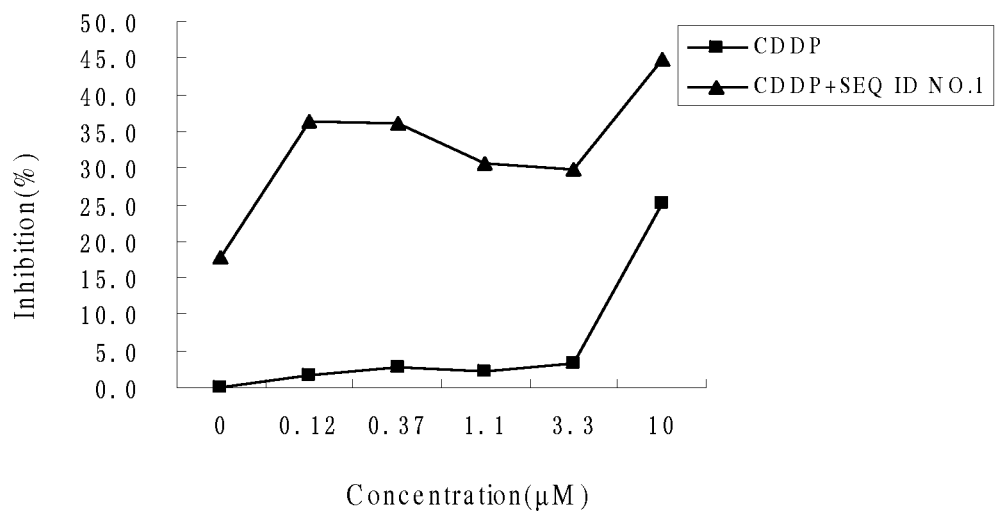
FIG. 3 SEQ ID NO.1 peptide cisplatin combination of tumor cells.

From FIG. 3, when cisplatin and SEQ ID NO.1 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 4

The Combined Effects of SEQ ID NO.2, SEQ ID NO.3 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, the mixture of first and SEQ ID NO.2, and the mixture of first and SEQ ID NO.3 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L, with 3 wells each concentration. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 4:
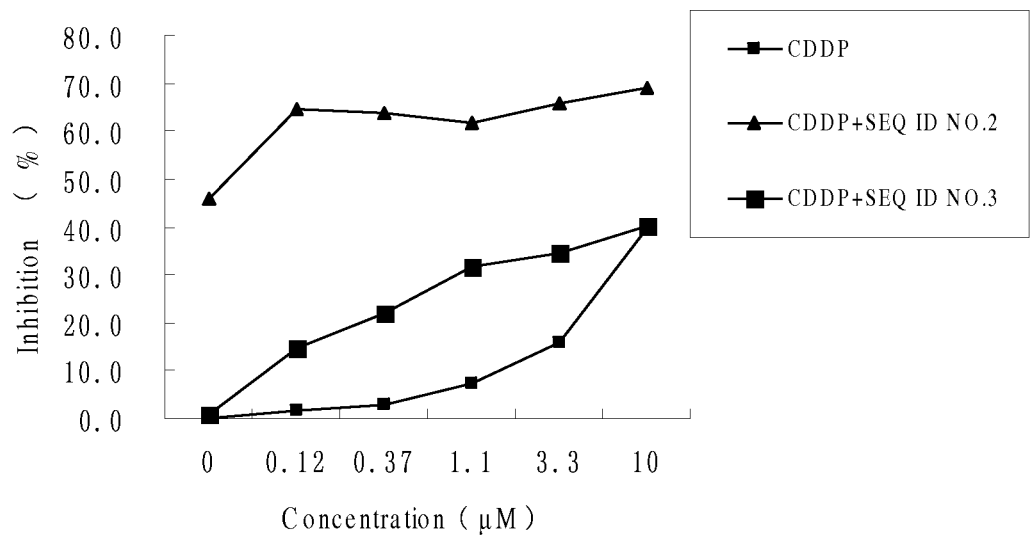
FIG. 4 SEQ ID NO.2 peptide, SEQ ID NO.3 peptides were used in combination with cisplatin to tumor cells results.

From FIG. 4, when cisplatin and SEQ ID NO.2 in combination as well as cisplatin and SEQ ID No. 3 in combination, their inhibition of HCT-116 cells was stronger than using cisplatin alone. So the peptides of the invention SEQ ID NO.2 or SEQ ID NO.3 can enhance the sensibility of cisplatin to Human colon cancer cell HCT-116 and increase the inhibition on it too.

Example 5

The Combined Effects of SEQ ID NO.4 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.4 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 5:
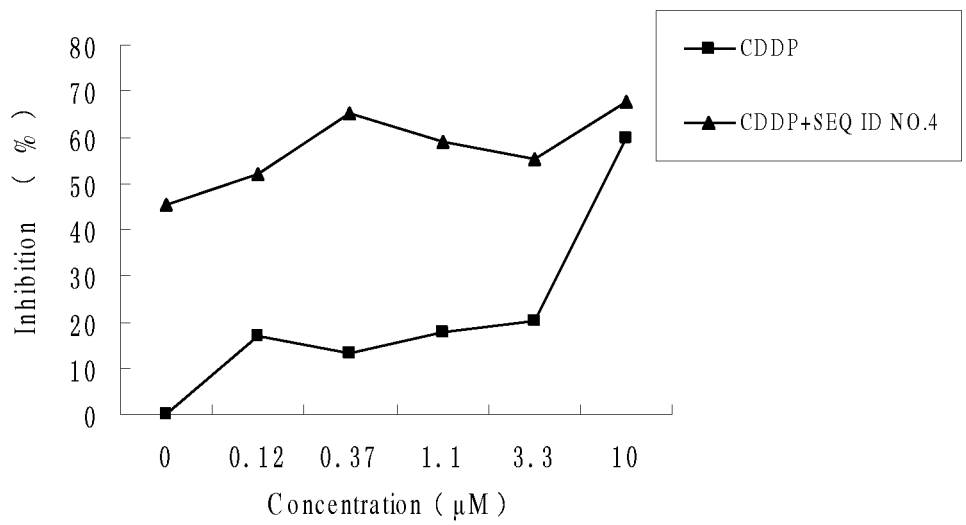
FIG. 5 SEQ ID NO.4 peptide cisplatin combination of tumor cells

According to FIG. 5, when cisplatin and SEQ ID NO.4 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 6

The Combined Effects of SEQ ID NO.5 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.5 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 6:
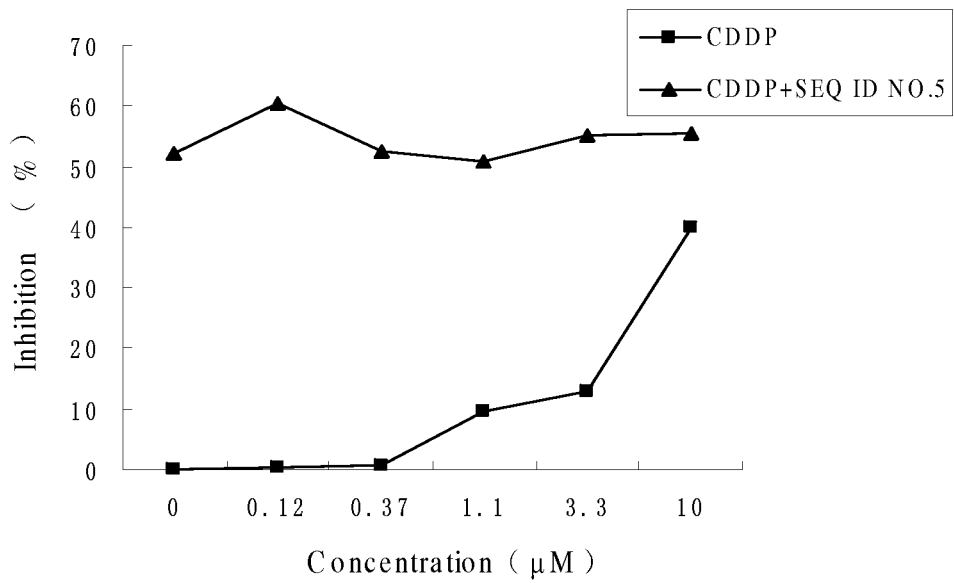
FIG. 6 SEQ ID NO.5 peptide cisplatin combination of tumor cells.

According to FIG. 6, when cisplatin and SEQ ID NO.5 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 7

The Combined Effects of SEQ ID NO.5 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.6 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 7:
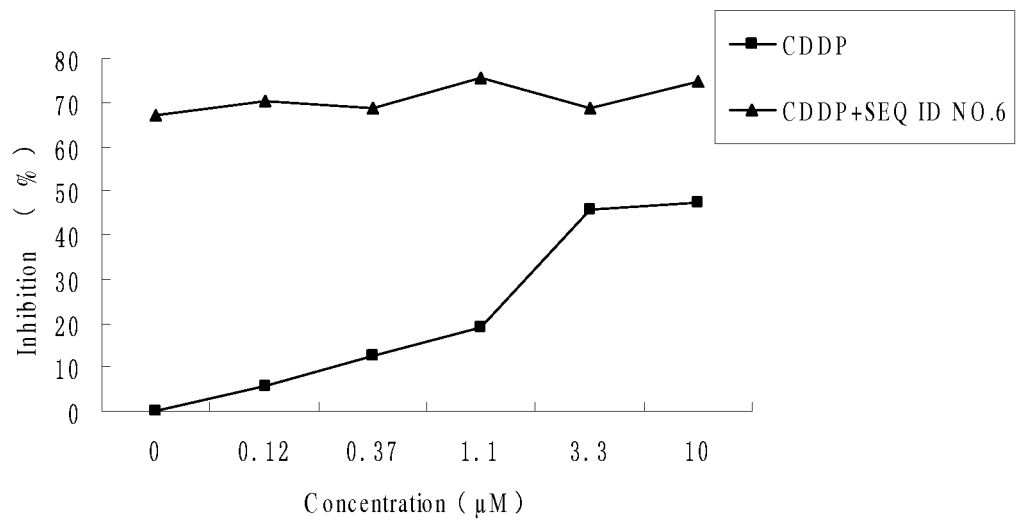
FIG. 7 SEQ ID NO.6 peptide cisplatin combination of tumor cells.

According to FIG. 7, when cisplatin and SEQ ID NO.6 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 8

The Combined Effects of SEQ ID NO.7 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.7 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 8:
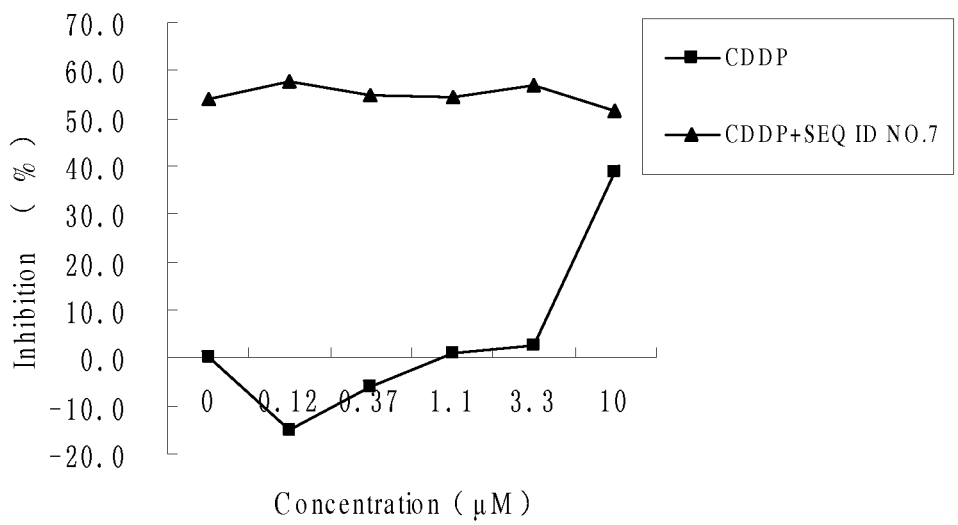
FIG. 8 SEQ ID NO.7 peptide cisplatin combination of tumor cells.

According to FIG. 8, when cisplatin and SEQ ID NO.7 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 9

The Combined Effects of SEQ ID NO.8 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.8 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 9:
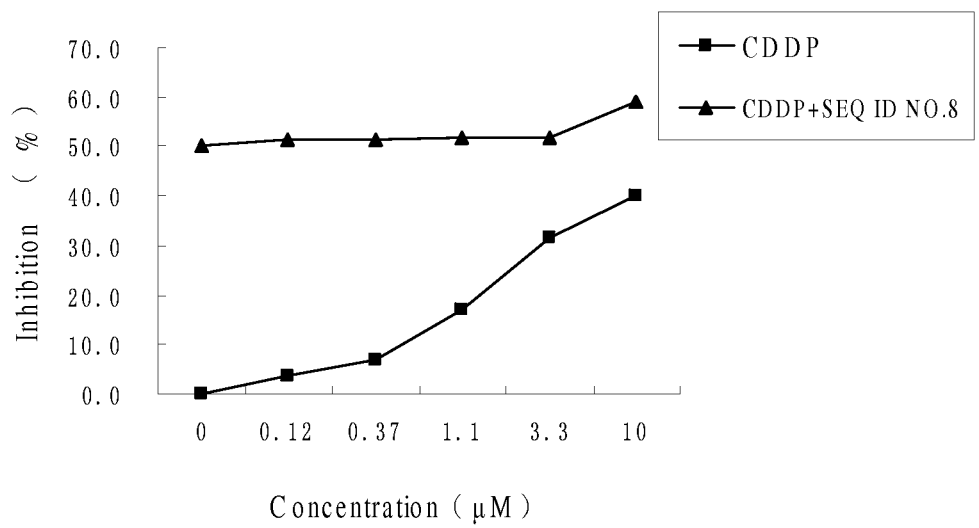
FIG. 9 SEQ ID NO.8 peptide cisplatin combination of tumor cells.

According to FIG. 9, when cisplatin and SEQ ID NO.8 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 10

The Combined Effects of SEQ ID NO.9 Peptide and Cisplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Cisplatin, and the mixture of the first and SEQ ID NO.9 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(*OD* in control group−*OD* in experimental group)/*OD* in control group×100%

2. Experimental Results

Figure 10:
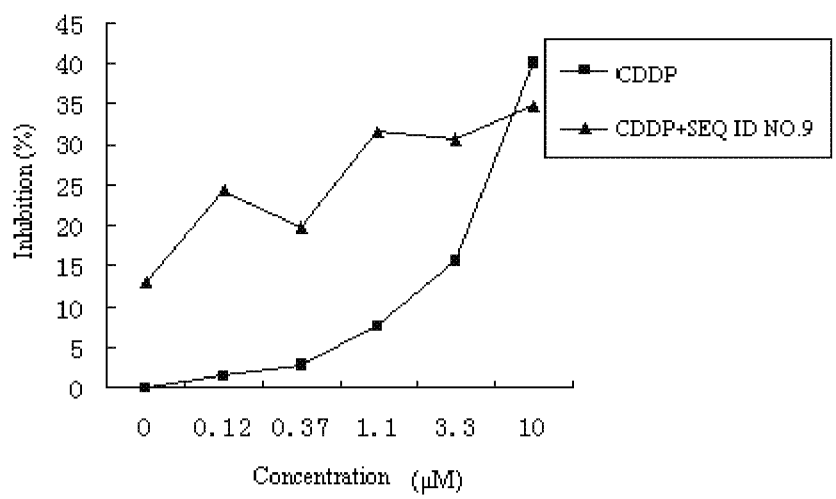
FIG. 10 SEQ ID NO.9 peptide cisplatin combination of tumor cells

According to FIG. 10, when cisplatin and SEQ ID NO.9 plus, their inhibition effect on HCT-116 cells was stronger than the separate use of cisplatin. So the peptides of the invention can enhance the sensibility of cisplatin to Human colon cancer cell HCT-116 and increase the inhibition on it too.

Example 11

The Combined Effects of SEQ ID NO.5 Peptide and Oxaliplatin on Cancer Cells with MTT Colorimetry 1. Experimental Method The human HCT116 cell line which was bought from ShangHai cell bank of Chinese academy of Science were suspended in RPMI1640 medium with 10% heart-inactivated fetal bovine serum, seeded into 96-well plate at a density of 5000-10000 cells per well, and cultured at 37° C. with 5% $CO_2$ under saturated humidity for 24 h. Oxaliplation, and the mixture of the first and SEQ ID NO.5 were respectively added into wells, that the concentration gradient of them in every mixture always was 90 μmol/L, 30 μmol/L, 10 μmol/L, 3.3 μmol/L, 1.1 μmol/L, 0.37 μmol/L, 0.12 μmol/L, 0 μmol/L. The final concentrations in every well were all 20 μmol/L, and each concentration set three wells. The medium were added MTT (5 mg/mL) after continuously cultured 20 h and sucked out the medium 4 h later. Adding 150 μmol/L DMSO in each well, the medium were shaken for 10 min until the violet crystal was completely soluble. The absorbance (OD) was determined by ELISA Reader at 570 nm.

The inhibitive rate=(OD in control group−OD in experimental group)/OD in control group×100%

2. Experimental Results

Figure 11:
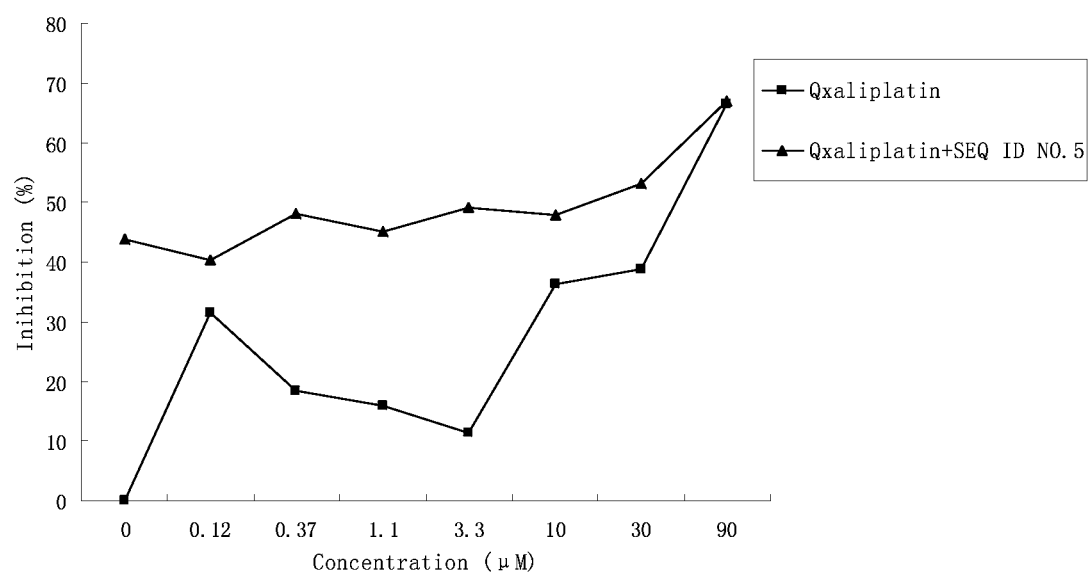
FIG. 11 SEQ ID NO.5 peptide and oxaliplatin combination on tumor cells

According to FIG. 11, when oxaliplation and SEQ ID NO.5 plus, their inhibition effect on HCT-116 cells was stronger than the separate use of oxaliplation. So the peptides of the invention can enhance the sensibility of oxaliplation to Human colon cancer cell HCT-116 and increase the inhibition on it too.

Example 12

The Effect of Anti-Cancer of SEQ ID NO.5 Peptide In Vivo

1. Experimental Method

Weighted 18-22 g BALB/c male mouse which were bought from Beijing Vital Riven laboratory animal limited company were used in experiment. Colon tumor 26, the cancer tissue was grinded to cellular suspension with 0.85% saline at a proportion of 1:10, and using aseptic operation subcutaneously inoculated tumor on the animal right flank armpit with 0.2 mL each animal. After 24 h, the mouse was injected intraperitoneally with SEQ ID NO.5 peptide once a day for 10 times. Cisplatin was injected intraperitoneally once every other day for 5 times. SEQ ID NO.5 peptide and cisplatin dissolved in 0.85% saline, and been injected intraperitoneally at a concentration of 0.2 mL/20 g (weight). The control group (0.85% saline), diverse amounts group of SEQ ID NO.5 peptide, cisplatin group, and diverse amounts group of SEQ ID NO.5 peptide plus cisplatin were set in experimental. After 11 days (Day 11), all mice were weighed and sacrificed. The tumors were excised and weighed. The tumorous inhibitive rate was counted by following equation, dealt with statistics, and estimated if having the significantly differences or not.

The tumorous inhibitive rate=(the mean control tumor weight−the mean treated tumor weight)/The mean control tumor weight*100%

Combine index (CI), CI=AB/(A×B). AB is the T/C of the combined effects of two drugs, A, B either is the T/C of the effect of one drug (when CI<1, these two drugs have combination).

2. Experimental Result

The inhibition of anti-cancer on colon tumor 26 induced by combined drugs, SEQ ID NO.5 peptide and cisplatin depends on the dosage. 10 mg/kg, 20 mg/kg, 40 mg/kg of SEQ ID NO.5 peptide combined with 1 mg/kg of cisplatin have varying degrees of antitumor effects, that combined administration of the inhibition rates were 51%, 61% and 66% ($P<0.01$) and the CI were 0.88, 0.73 and 0.79 in that order. The experimental results show that the synergies between the two, the 20 mg/kg combined treatment group showed significant synergy (Table 2).

Vivo experimental results show that, the growth inhibition effect of SEQ ID NO.5 peptide combined with cisplatin on mice transplanted tumor of colon tumor 26 was dose dependent. SEQ ID NO.5 peptide and cisplatin combined with medication has a synergistic effect.

TABLE 1 the physical and chemical properties of SEQ ID NO. 1-SEQ ID NO. 10 peptide

| | Properties | SEQ ID NO. 1 | SEQ ID NO. 2 | SEQ ID NO. 3 | SEQ ID NO. 4 | SEQ ID NO. 5 | SEQ ID NO. 6 | SEQ ID NO. 7 | SEQ ID NO. 8 | SEQ ID NO. 9 | SEQ ID NO. 10 |
|---|---|---|---|---|---|---|---|---|---|---|---|
| Physical property | Color | White or almost white powder, moisture absorption | White or almost white powder, moisture absorption | White or almost white powder, moisture absorption | White or almost white powder, moisture absorption | White or almost white powder, moisture absorption | White or almost white powder, moisture absorption | White or almost white powder, moisture absorption | White or almost white powder, moisture absorption | White or almost white powder, moisture absorption | White or almost white powder, moisture absorption |
| | solution | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. | Soluble in water, ACN, glacial Acetic Acid, etc. |
| Chemical property | Ninhydrin Test | Color reaction, red | Color reaction, red | Color reaction, red | Color reaction, red | Color reaction, red | Color reaction, red | Color reaction, red | Color reaction, red | Color reaction, red | Color reaction, red |
| | HPLC | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance | using C18 column HPLC, the retention time of the product is in accord with one of reference substance |
| | MS | 480.57 | 1671.96 | 1758.06 | 1786.11 | 2074.48 | 2036.43 | 2102.53 | 2074.54 | 1979.33 | 2051.4 |

TABLE 2

The combination of SEQ ID NO. 5 peptide and cisplatin to mice colon cancer 26

| Groups | Dosage (mg/kg) | Administered route and Frequency | Aniamal number start | Aniamal number end | Changes of Weight (g) start | Changes of Weight (g) end | $\bar{x} \pm s$ (g) | The inhibitive rate (%) | P value | CI value |
|---|---|---|---|---|---|---|---|---|---|---|
| Control |  | ipx10 | 10 | 10 | 20.1 | 21.44 | 2.47 ± 0.31 | — | — |  |
| Cisplatin | 1 | ipx 5 | 10 | 10 | 19.54 | 18.78 | 1.39 ± 0.39 | 44 | <0.01 |  |
| SEQ ID NO. 5 peptide | 10 | ipx10 | 10 | 10 | 21.55 | 20.54 | 2.63 ± 0.49 | 0 | >0.05 |  |
|  | 20 | ipx10 | 10 | 10 | 19.48 | 19.01 | 2.35 ± 0.42 | 5 | >0.05 |  |
|  | 40 | ipx10 | 10 | 10 | 20.00 | 19.01 | 1.91 ± 0.43 | 23 | >0.01 |  |
| SEQ ID NO. 5 peptide + cisplatin | 10 + 1 | ipx10 + ipx 5 | 10 | 10 | 20.38 | 19.62 | 1.21 ± 0.29 | 51 | <0.01 | 0.88 |
|  | 20 + 1 | ipx10 + ipx 5 | 10 | 10 | 19.35 | 18.93 | 0.97 ± 0.32 | 61 | <0.01 | 0.73 |
|  | 40 + 1 | ipx10 + ipx 5 | 10 | 10 | 20.05 | 18.62 | 0.85 ± 0.25 | 66 | <0.01 | 0.79 |

```
SEQUENCE LISTING
                                                        SEQ ID NO. 1
Ile Val His Asn

SEQ ID NO. 2
Ile Val His Asn Gly Phe Arg Arg Gly Trp Met Trp Gly Gly

SEQ ID NO. 3
Ile Val His Asn Gly Phe Arg Arg Gly Trp Met Trp Ala Glu

SEQ ID NO. 4
Ile Val His Asn Gly Phe Arg Arg Gly Trp Met Trp Val Glu

SEQ ID NO. 5
Met Phe Ile Val His Asn Glu Leu Arg Arg Gly Trp Met Trp Ala Glu

SEQ ID NO. 6
Met Phe Ile Val His Asn Gly Phe Arg Arg Gly Trp Met Trp Ala Glu

SEQ ID NO. 7
Met Phe Ile Val His Asn Glu Leu Arg Arg Gly Trp Met Trp Val Glu

SEQ ID NO. 8
Met Phe Ile Val His Asn Glu Leu Arg Arg Gly Trp Met Trp Val Thr

SEQ ID NO. 9
Met Phe Ile Val His Asn Gly Phe Arg Arg Gly Glu Met Trp Ala Glu

SEQ ID NO. 10
Met Phe Ile Val His Asn Glu Phe Arg Arg Gly Glu Met Trp Ala Glu
```

---

What is claimed is:

1. A peptide for killing cancer cells is selected from a group of peptides whose amino acid sequences are SEQ ID NO.2, SEQ ID NO.3, SEQ ID NO.4, SEQ ID NO.5, SEQ ID NO.6, SEQ ID NO.7, SEQ ID NO.8, SEQ ID NO.9 or SEQ ID NO.10.

* * * * *